United States Patent
Yasueda et al.

(10) Patent No.: US 6,274,609 B1
(45) Date of Patent: Aug. 14, 2001

(54) AQUEOUS LIQUID PHARMACEUTICAL COMPOSITION CONTAINING AS MAIN COMPONENT BENZOPYRAN DERIVATIVE

(75) Inventors: Shinichi Yasueda, Takarazuka; Tadashi Terai, Kobe; Takahiro Ogawa, Nishinomiya; Yoshinori Ii, Mishima-gun, all of (JP)

(73) Assignees: Ono Pharmaceutical Co., Ltd.; Senju Pharmaceutical Co., Ltd., both of Osaka (JP)

( * ) Notice: Subject to any disclaimer, the term of this patent is extended or adjusted under 35 U.S.C. 154(b) by 0 days.

(21) Appl. No.: 09/463,211
(22) PCT Filed: Jul. 15, 1998
(86) PCT No.: PCT/JP98/03172
  § 371 Date: Jan. 21, 2000
  § 102(e) Date: Jan. 21, 2000
(87) PCT Pub. No.: WO99/04790
  PCT Pub. Date: Feb. 4, 1999

(30) Foreign Application Priority Data

Jul. 23, 1997 (JP) .................................................. 9-196771

(51) Int. Cl.[7] .................................................. A61K 31/41
(52) U.S. Cl. .................................................. 514/382
(58) Field of Search .............................. 514/382

(56) References Cited

U.S. PATENT DOCUMENTS 5,976,760 * 3/1999 Sasatani et al. ..................... 424/494

FOREIGN PATENT DOCUMENTS 0641569   3/1995   (EP) .
96/41628  12/1996  (WO) .

OTHER PUBLICATIONS

Database WPI, Section Ch, Week 9621, Derwent Publications Ltd., London, GB; Class A96, AN 96–205438, XP002081469 & JP 08 073353 A (Ono Pharmaceutical) Mar. 19, 1996.

* cited by examiner

Primary Examiner—James H. Reamer
(74) Attorney, Agent, or Firm—Wenderoth, Lind & Ponac L.L.P.

(57) ABSTRACT

In order to promote solubilization or suspension of 4-oxo-8-[4-(4-phenylbutoxy)benzoylamino]-2-(tetrazol-5-yl)-4H-1-benzopyran or its hydrate (pranlukast) in water, at least one component selected from surfactants, water-soluble cellulose derivatives and water-soluble vinyl polymers is formulated together with pranlukast. Thus, it is possible to provide an aqueous liquid pharmaceutical composition containing higher concentration of pranlukast and having good properties.

37 Claims, 2 Drawing Sheets

AQUEOUS LIQUID PHARMACEUTICAL COMPOSITION CONTAINING AS MAIN COMPONENT BENZOPYRAN DERIVATIVE

FIELD OF THE INVENTION

The present invention relates to a pharmaceutical composition comprising as a main component 4-oxo-8-[4-(4-phenylbutoxy)benzoylamino]-2-(tetrazol-5-yl)-4H-1-benzopyran or its hydrate. In particular, it relates to an aqueous liquid pharmaceutical composition containing the benzopyran derivative or its hydrate in higher concentration and having good properties.

BACKGROUND OF THE INVENTION

4-Oxo-8-[4-(4-phenylbutoxy)benzoylamino]-2-(tetrazol-5-yl)-4H-1-benzopyran is an antagonist toward leukotrienes (LTC4, LTD4, LTE4) and is known to be a medicine having excellent pharmacological activities on various allergic diseases including asthma (JP-A 61-50977). Its ½ hydrate is called as "pranlukast" and is utilized as an anti-allergic medicine. Then, in the field of ophthalmology, it has been proposed to apply such a medicine to allergic eye diseases such as vernal keratoconjunctivitis, etc.

In general, for preparing an aqueous liquid pharmaceutical composition such as water-soluble eye drops, it is considered that a pharmacologically active component should be present in concentration of about 0.01 to 0.1%. However, 4-oxo-8-[4-(4-phenylbutoxy)benzoylamino]-2-(tetrazol-5-yl)-4H-1-benzopyran and its hydrate (hereinafter, they are referred to as "pranlukast" all together, unless otherwise stated) have very low water-solubility, which makes every difficult to prepare a useful aqueous liquid pharmaceutical composition thereof. Then, the use of polyvinyl pyrrolidone and β-cyclodextrin has been proposed to solubilize pranlukast (JP-A 8-73353).

However, even if polyvinyl pyrrolidone, which is a material known to have strongest solubilization power, is used, pranlukast dissolves in water in concentration of, at highest, about 0.01%.

OBJECTS OF THE INVENTION

The main object of the present invention is to promote solubilization or suspension of pranlukast in water, thereby providing an aqueous liquid pharmaceutical composition containing higher concentration of pranlukast and having good properties.

This object as well as other objects and advantages of the present invention will become apparent to those skilled in the art from the following description with reference to the attached drawings.

SUMMARY OF THE INVENTION

Figure 1:
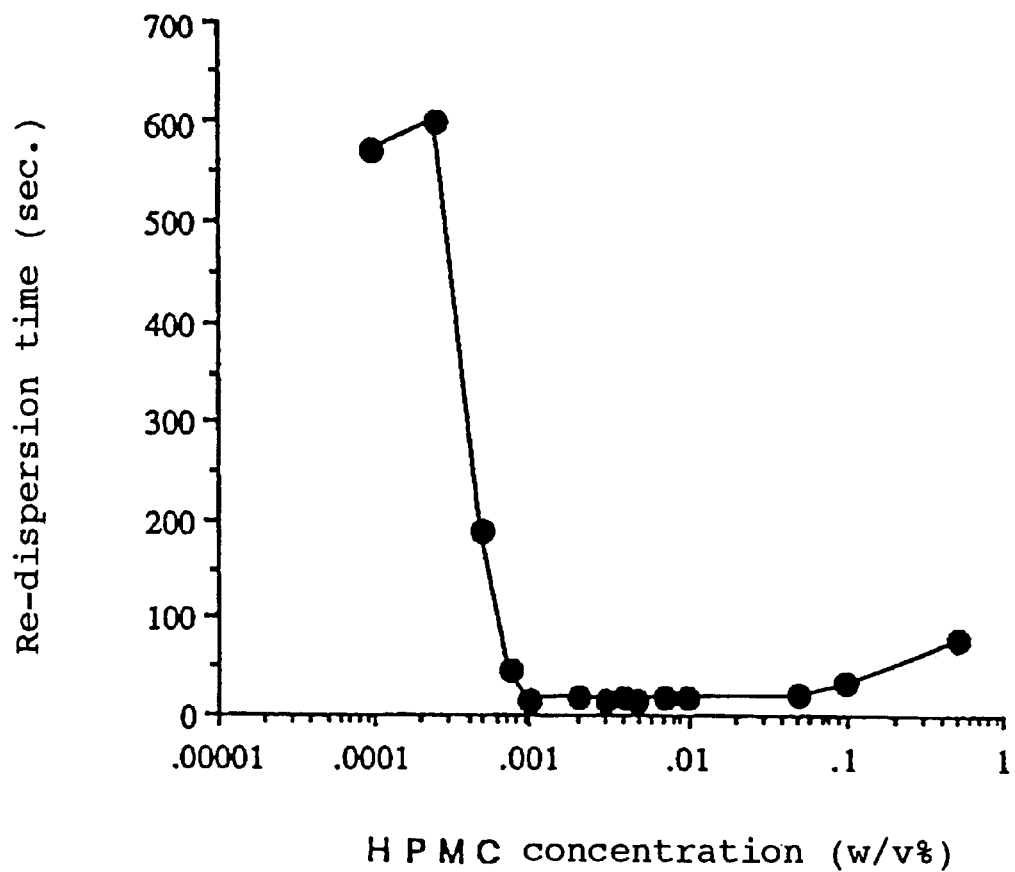
FIG. 1 is a graph illustrating the relation between hydroxypropylmethyl cellulose (HPMC) concentration and time required for re-dispersion of pranlukast.

The present inventors have extensively studied to promote solubilization or suspension of pranlukast in water and, consequently, have found that the desired solubilization or suspension can be obtained by using at least one component selected from surfactants and specific high-molecular weight substances. Thus, the present inventors have succeeded in preparing the desired aqueous liquid pharmaceutical composition containing higher concentration of pranlukast and having good properties, and have completed the present invention.

That is, according to the present invention, there is provided an aqueous liquid pharmaceutical composition which comprises 4-oxo-8-[4-(4-phenylbutoxy)benzoylamino]-2-(tetrazol-5-yl)-4H-1-benzopyran or its hydrate and at least one component selected from surfactants, water-soluble cellulose derivatives and water-soluble vinyl polymers.

In particular, one aspect of the aqueous liquid pharmaceutical composition of the present invention is an aqueous solution containing pranlukast and a surfactant. Preferably, the composition further contains a stabilizer.

Another aspect of the aqueous liquid pharmaceutical composition of the present invention is an aqueous suspension containing pranlukast and at least one component selected from the group consisting of water-soluble cellulose derivatives and water-soluble vinyl polymers. Optionally, the suspension may further contain a surfactant. Preferably, the suspension contains a relatively small amount of a surfactant together with the water-soluble high-molecular weight substance.

These aqueous liquid pharmaceutical compositions have good re-dispersibility over a long time and are stable. In addition, they can contain higher concentration of pranlukast. Then, they can be useful as eye drops, nasal drops, injectable preparations, internal medicine and the like and can be used as an eosinocyte infiltration inhibitor.

DETAILED DESCRIPTION OF THE INVENTION

4-Oxo-8-[4-(4-phenylbutoxy)benzoylamino]-2-(tetrazol-5-yl)-4H-1-benzopyran or its hydrate to be used in the present invention is not specifically limited but its ½ hydrate available from Ono Pharmaceutical Co., Ltd. as "pranlukast" is suitable for the present invention.

The amount of pranlukast to be formulated in the composition is not specifically limited but, in case of an aqueous solution, it is formulated in an amount of 0.2 w/v % or less, normally, 0.001 to 0.2 w/v %, preferably 0.005 to 0.1 w/v % based on the total weight of the composition and, in case of an aqueous suspension, 0.01 to 5.0 w/v %, preferably 0.1 to 2.0 w/v % based on the total weight of the composition, in terms of its ½ hydrate.

The surfactants to be used are at least one member selected from nonionic surfactants, cationic surfactants and anionic surfactants. As the nonionic surfactants, it is preferred to use those having HLB of 10 to 18. Examples of the nonionic surfactants include polyoxyethylene sorbitan fatty acid ester (e.g., Polysorbate 80, Polysorbate 60, Polysorbate 40, etc.), polyoxyethylene hydrogenated castor oil (e.g., polyoxyethylene hydrogenated castor oil 60, polyoxyethylene hydrogenated castor oil 50, polyoxyethylene castor oil 40, etc.), polyoxyethylene alkylphenyl formaldehyde condensate (e.g., Tyloxapol, etc.), polyoxyethylene polyoxypropylene block copolymer (e.g., Poloxamer 188, Poloxamer 403, etc.) and sucrose ester of fatty acid (e.g., Ryutosugar ester P-1570 and S-1570 manufactured by Mitsubishi Chemical Foods), among others.

Examples of the cationic surfactants include quaternary ammonium salt (e.g., benzalkonium chloride, etc.), among others. Examples of the anionic surfactants include alkyl sulfate (e.g., sodium lauryl sulfate, etc.), among others.

The surfactant can be used alone or in combination of two or more thereof and, normally, in case of an aqueous solution, the surfactant(s) are formulated in an amount of 0.5 to 8 w/v %, preferably 1 to 5 w/v %, more preferably 2 to 4 w/v % based on the total weight of the composition. And, in this case, the proportion of the surfactant(s) to pranlukast is such that 5 to 100 parts, preferably 10 to 60 parts by weight of the surfactant(s) are formulated per 1 part of pranlukast (½ hydrate).

In case that the composition is an aqueous suspension, optionally, the surfactant(s) are formulated in an amount of 0.0001 to 0.2 w/v %, preferably 0.001 to 0.2 w/v %, more preferably 0.01 to 0.2 w/v % based on the total weight of the composition together with the water-soluble high-molecular weight substance as described hereinafter. And, in this case, the proportion of the surfactant(s) to pranlukast is such that 0.0001 to 0.2 part, preferably 0.001 to 0.2 part, more preferably 0.01 to 0.2 part by weight of the surfactant(s) are formulated per 1 part of pranlukast (½ hydrate).

In the present invention, when the composition is in the form of an aqueous solution, normally, pH of the composition is adjusted to 6 or higher, preferably 6 to 9, more preferably 6 to 8. Further, in addition to the surfactants, it is preferred to formulate at least one stabilizer selected from anti-oxidants and chelating agents in an amount of about 0.001 to 0.1 w/v %, thereby improving stability of pranlukast.

As such stabilizers, there are, for example, anti-oxidants such as butylated hydroxytoluene, butylated hydroxyanisole, etc. and chelating agents such as sodium edetate, etc. They can be used alone or in combination of two or more thereof.

The water-soluble cellulose derivatives used in the present invention include at least one member selected from methylcellulose, carboxymethylcellulose, hydroxypropyl cellulose, hydroxyethyl cellulose, and hydroxypropylmethyl cellulose.

The water-soluble vinyl polymers used in the present invention include at least one member selected from polyvinyl pyrrolidone K25, polyvinyl pyrrolidone K30, polyvinyl pyrrolidone K90, polyvinyl alcohol and carboxyvinyl polymer.

These water-soluble high-molecular weight substances can be used alone or in combination of two or more thereof.

As described above, these water-soluble high-molecular weight substances can be used together with one or more surfactants, thereby further improving re-dispersibility of the aqueous suspension, in particular, after storage.

In the present invention, the water-soluble cellulose derivatives and the water-soluble vinyl polymers function, in particular, as a suspending agent of the aqueous liquid pharmaceutical composition in the form of a suspension. Then, they are formulated in an amount of 0.00001 to 0.1 w/v %, preferably 0.00005 to 0.05 w/v % based on the total weight of the composition. And, the proportion of the water-soluble high-molecular weight substance(s) topranlukast is such that 0.0001 to 0.1 part by weight, preferably 0.0005 to 0.02 part by weight of the water-soluble high-molecular weight substance(s) are formulated per 1 part by weight of pranlukast (½ hydrate).

In a liquid pharmaceutical composition, such suspending agent is generally used in concentration ranging from 0.1 to 4 w/v % based on the total weight of the composition. In view of this, it is very surprising that the suspending agent functions even in such a small amount as in the present invention.

When the aqueous liquid pharmaceutical composition is in the form of a suspension, pH of the composition may be within, for example, the range normally employed for eye drops (e.g., pH 4 to 9, preferably pH 5 to 8).

If necessary, the aqueous liquid pharmaceutical composition may further contain suitable additives, for example, an isotonic agent such as inorganic salt (e.g., sodium chloride, boric acid, potassium chloride, etc.) and polyhydric alcohol (e.g., glycerin, mannitol, sorbitol, etc.); a buffer solution such as borate buffer solution, phosphate buffer solution, acetate buffer solution, citrate buffer solution, Tris buffer solution, etc. and buffer agent such as amino acid (e.g., glutamic acid, $\epsilon$-aminocapronic acid, etc.); a chelating agent such as sodium edetate, citric acid, etc.; a preservative such as quaternary ammonium salt (e.g., benzalkonium chloridie, benzethonium chloride, etc.), p-hydroxybenzoate (methyl p-hydroxybenzoate, ethyl p-hydroxybenzoate, propyl p-hydroxybenzoate, butyl p-hydroxybenzoate, etc.), sorbic acid, chlorobutanol, sodium edetate, boric acid, etc., and the like. Normally, an isotonic agent can be formulated in an amount of 0.5 to 6.5 w/v % based on the total weight of the composition. Likewise, 0.01 to 1.0 w/v % of a buffer and 0.001 to 0.1 w/v % of a chelating agent can be formulated based on the total weight of the composition.

The aqueous liquid pharmaceutical composition of the present invention can be prepared in the form of an aqueous solution or suspension such as eye drops, nasal drops, injectable preparations, internal medicine and the like according to a per se known method. For example, the composition can be prepared by adding the solubilizing agent and/or suspending agent, a buffer, an isotonic agent and a preservative to sterilized purified water and, if necessary, heating to dissolve them. The desired liquid pharmaceutical composition can be prepared by dissolving or suspending pranlukast in the resultant solution.

The aqueous liquid pharmaceutical composition of the present invention has eosinocyte infiltration inhibitory activity and is useful as an eosinocyte infiltration inhibitor. Then, it can be used for prophylaxis and therapy of seasonal or year-round allergic conjunctivitis, vernal keratoconjunctivitis, atopic keratoconjunctivitis, giant papillary conjunctivitis, contact blephroconjunctivits, keratitis, scleritis, uveitis, eye itch, allergic rhinitis, sneeze, nasal itching, nasal hypersensitivity, nasofrontal eczema, nasal obstruction and the like. In general, the composition is topically or systemically administered once to six times per day at a daily dosage of 20 to 100 $\mu$g/ml of pranlukast.

The present invention will be further illustrated by the following experiments and preparation examples, but the present invention is not limited to these preparation examples. In the following experiments and preparation examples, "pranlukast" used is the ½ hydrate and all the "percents" are by weight unless otherwise stated.

Experiment 1

Study of solubilizing agents of pranlukast

Method

Pranlukast (manufactured by Ono Pharmaceutical Co., Ltd.) was suspended in 0.1% borate buffer (pH 9 or 8) or 0.1% phosphate buffer (pH 8 or 7) at concentration of 0.1 w/v %. Likewise, pranlukast was suspended in each 0.5% solution of surfactants (polysorbate 80, polysorbate 60, polysorbate 40, polyoxyethylene hydrogenated castor oil 60, Tyloxapol, benzalkonium chloride, and sodium lauryl sulfate), water-soluble vinyl polymers (polyvinyl pyrrolidione K30, and polyvinyl alcohol), cyclodextrins ($\beta$-cyclodextrin, $\gamma$-cyclodextrin, and 2HP-$\beta$-cyclodextrin)

and caffeine in 0.1% phosphate buffer (pH 7) at concentration of 0.1 w/v %. Each suspension was filled in a glass ampoule and was shaken overnight (for about 15 hours) at 25° C. After shaking, the suspension was filtered through a membrane filter of 0.45 μm pore size and pranlukast in the filtrate was determined by HPLC.

Results

Solubility of pranlukast is shown in Table 1.

TABLE 1

| | Additives | pH | Solubility (μg/ml) |
|---|---|---|---|
| Buffers | 0.1% borate buffer | 9 | 129.3 |
| | 0.1% borate buffer | 8 | 38.4 |
| | 0.1% phosphate buffer | 8 | 72.5 |
| | 0.1% phosphate buffer | 7 | 2.4 |
| Surfactants | polysorbate 80 | 7 | 719.6 |
| | polysorbate 60 | 7 | 639.3 |
| | polysorbate 40 | 7 | 628.6 |
| | polyoxyethylene hydrogenated castor oil 60 | 7 | 408.1 |
| | Tyloxapol | 7 | 551.0 |
| | benzalkonium chloride | 7 | 174.5 |
| | sodium lauryl sulfate | 7 | 223.3 |
| Water-soluble vinyl polymers | polyvinyl pyrrolidone K30 | 7 | 159.9 |
| | polyvinyl alcohol | 7 | 99.2 |
| Cyclodextrin (control) | β-cyclodextrin | 7 | 105.2 |
| | γ-cyclodextrin | 7 | 94.9 |
| | 2HP-β-cyclodextrin | 7 | 107.5 |
| | caffeine (control) | 7 | 63.0 |

As seen from Table 1, solubility of pranlukast in the buffer was increased with the rise of pH. Further, solubility of pranlukast was increased by addition of the surfactants, water-soluble vinyl polymers, cyclodextrin and caffeine.

Experiment 2

Relation between solubilization of pranlukast and pH, when using polysorbate 80 as the solubilizing agent Method Polysorbate 80 was dissolved in 0.1% phosphate buffer and/or 0.1% acetate buffer at concentration of 0.5%. Pranlukast (manufactured by Ono Pharmaceutical Co., Ltd.) was suspended in the resultant solution at concentration of 0.2% and pH was adjusted to 5 to 8 with sodium hydroxide or hydrochloric acid. Each suspension was filled in a glass ampoule and shaken overnight (for about 15 hours) at 25° C. After shaking, the suspension was filtered with a membrane filter of 0.22 μm pore size and pranlukast in the filtrate was determined by HPLC.

Results

Solubility of pranlukast is shown in Table 2.

As the rise in pH, solubility of pranlukast was increased. A difference in buffers was scarcely observed.

TABLE 2

| | Solubility of pranlukast (μg/ml) pH | | | |
|---|---|---|---|---|
| Buffer | 5 | 6 | 7 | 8 |
| 0.1% phosphate buffer (pH after shaking) | 92.6 (5.28) | 252.9 (6.00) | 719.6 (6.98) | 1147.4 (7.86) |

TABLE 2-continued

| | Solubility of pranlukast (μg/ml) pH | | | |
|---|---|---|---|---|
| Buffer | 5 | 6 | 7 | 8 |
| 0.1% acetate buffer (pH after shaking) | 87.2 (5.06) | 292.4 (6.12) | — | — |

Experiment 3

Relation between concentration of polysorbate 80 and polyoxyethylene hydrogenated castor oil 60, and solubility of pranlukast Method Polysorbate 80 or polyoxyethylene hydrogenated castor oil 60 (hereinafter abbreviated as HCO-60) was dissolved in 0.1% phosphate buffer at concentration of 1.0%, 2.0%, 3.0% or 4.0%. Pranlukast (manufactured by Ono Pharmaceutical Co., Ltd.) was suspended in the resultant solution at concentration of 0.2%. Each suspension was filled in a glass ampoule and shaken overnight (for about 15 hours) at 25° C. After shaking, the suspension was filtered with a membrane filter of 0.22 μm pore size and pranlukast in the filtrate was determined by HPLC.

Results

Regarding each nonionic surfactant at each concentration, solubility of pranlukast is shown in Table 3.

TABLE 3

| | | Solubility of pranlukast (μg/ml) Concentration of additive (%) | | | |
|---|---|---|---|---|---|
| Additive | pH | 1.0 | 2.0 | 3.0 | 4.0 |
| Polysorbate 80 | 7 | 1052.1 | 1483.6 | 1636.4 | 1747.4 |
| HCO-60 | 7 | 718.9 | 1119.9 | 1370.7 | 1525.3 |

As seen from Table 3, solubility of pranlukast was increased as increase in the amount of polysorbate 80 and polyoxyethylene hydrogenated castor oil 60.

Experiment 4

Test for stability of aqueous solution of pranlukast

Method

According to the formulations in Table 4, solutions A to F were prepared. Each solution was filled in a 5 ml-glass ampoule and stored at 60° C. for 2 weeks. After 2 weeks, pranlukast in the solution was determined by HPLC and its residual rate was calculated.

TABLE 4

| | Formulation | | | | | |
|---|---|---|---|---|---|---|
| Component | A | B | C | D | E | F |
| pranlukasut | 0.1 g | 0.1 g | 0.1 g | 0.1 g | 0.1 g | 0.1 g |
| polysorbate 80 | — | — | — | 4.0 g | 4.0 g | 4.0 g |
| Tyloxapol | 4.0 g | 4.0 g | — | — | — | — |
| HCO-60* | — | — | 4.0 g | — | — | — |
| boric acid | — | 1.9 g | — | — | — | — |
| BHT** | — | — | — | — | 0.01 g | — |

TABLE 4-continued

| | Formulation | | | | | |
|---|---|---|---|---|---|---|
| Component | A | B | C | D | E | F |
| sodium edetate | — | — | — | — | — | 0.01 g |
| sodium di-hydrogen phosphate | 0.1 g | — | 0.1 g | 0.1 g | 0.1 g | 0.1 g |
| benzalkonium chloride | 0.005 g | — | — | — | — | — |
| 0.1 N sodium hydroxide | q.s. | q.s. | q.s. | q.s. | q.s. | q.s. |
| sterilized purified water | up to total 100 ml | up to total 100 ml | up to total 100 ml | up to total 100 ml | upt to total 100 ml | up to total 100 ml |
| pH | 7.0 | 7.0 | 7.0 | 7.0 | 7.0 | 7.0 |

*polyoxyethylene hydrogenated castor oil 60
**butylated hydroxytoluene

Results

The residual rate of pranlukast is shown in Table 5.

TABLE 5

| | Residual rate (%) | | | | | |
|---|---|---|---|---|---|---|
| | A | B | C | D | E | F |
| Immediately after preparation | 100.0 | 100.0 | 100.0 | 100.0 | 100.0 | 100.0 |
| After two weeks | 99.6 | 99.4 | 98.9 | 85.0 | 97.5 | 95.1 |

As seen from Table 5, when Tyloxapol and polyoxyethylene hydrogenated castor oil 60 were used as the solubilizing agents (formulations A, B and C), the residual rate of pranlukast was more than 98% and was stable. When polysorbate 80 was used as the solubilizing agent (formulation D), although stability of pranlukast was somewhat lowered in comparison with the other surfactants, stability of more than 95% was obtained by adding the stabilizer, BHT or sodium edetate (formulations E and F).

In each solution, no deposit of any insoluble material was observed.

Experiment 5

Relation between concentration of suspending agent and re-dispersibility

Method

Solutions of hydroxyporpylmethyl cellulose (hereinafter abbreviated as HPMC) ranging in concentration from 0.0001 to 0.5% were prepared and pranlukast was added thereto at concentration of 0.5%. After standing at 25° C. for 4 days, time required for re-dispersion was measured with a variable mix rotor VMR-5 (60 rpm, manufactured by Iuch Co., Ltd.)

Results

FIG. 1 illustrates the relation between HPMC concentration and time required for re-dispersion.

As seen from FIG. 1, when concentration of HPMC (X-axis) was within the range of 0.00075 to 0.1%, time required for re-dispersion of suspending particles of pranlukast (Y-axis) was relatively shorter. In addition, no aggregation or caking of suspending particles of pranlukast was observed within this concentration range.

Experiment 6

Test for eye irritation

Method

According to the formulations of Table 6, aqueous solutions (formulations G and H) and suspension (formulation J) of pranlukast were prepared. Eye drops of each solution or suspension were applied to Japanese white male rabbits 8 times per day (0.05 ml/once) and eye irritation was evaluated by the naked eye according to Draize method.

TABLE 6

| | G | H | J |
|---|---|---|---|
| pranlukast | 0.1 g | 0.1 g | 1.0 g |
| polysorbate 80 | 4.0 g | — | — |
| polyoxyethylene hydrogenated castor oil 60 | — | 4.0 g | — |
| hydroxypropylmethyl cellulose | — | — | 0.005 g |
| butylated hydroxytoluene | 0.01 g | — | — |
| sodium dihydrogen phosphate | 0.1 g | 0.1 g | — |
| sodium acetate | — | — | 0.1 g |
| sodium chloride | 0.9 g | 0.9 g | 0.9 g |
| methyl p-hydroxybenzoate | — | — | 0.026 g |
| propyl p-hydroxybenzoate | — | — | 0.014 g |
| 0.1 N sodium hydroxide | q.s. | q.s. | — |
| 0.1 N hydrochloric acid | — | — | q.s. |
| serilized purified water | up to 100 ml | up to 100 ml | up to 100 ml |
| pH | 7.0 | 7.0 | 5.0 |

Results

No eye irritation was observed in all the formulations.

Experiment 7

Conjunctival eosinocyte infiltration inhibitory activity

Method

1. Animals

Hartley male guinea pigs (body weight: about 300 to 500 g) purchased from Japan SLC were used. The animals were bred under conditions of a temperature of 23±2° C. and humidity of 55±15%. They were maintained on pellets (radiation sterilized Labo G standard manufactured by Nihon Nosan Kogyo) and sterilized water for animals ad libitum.

2. Test medicine

Pranlukast was suspended in a vehicle containing 0.1% of sodium dihydrogen phosphate, 0.9% of sodium chloride and 0.1% polysorbate 80 (pH 7) at concentration of 1.0%. As a control, physiological saline solution was used.

3. Procedure

The guinea pigs were sensitized by administering a mixture of 10 μg of ovalbumin (hereinafter referred to as OA) and 30 mg of aluminum hydroxide gel intraperitoneally. 14 Days after sensitization, 10 μl of 2.5% OA antigen solution was instilled in both eyes of the guinea pigs to cause conjunctivitis (primary challenge). Likewise, 24 hours after the primary challenge, 2.5% OA antigen solution was instilled to cause conjunctivitis again (secondary challenge).

After 6 hours, each guinea pig was slaughtered, the upper and lower lids were removed from the periosteum and the lids together with the eyeball were extracted. According to a conventional manner, the eyeball was fixed and embedded in paraffin to prepare a specimen for optical microscopic examination and cut into slices 3 μm in thickness. The resultant pathological slice was stained by Luna stain, its part where most infiltration of conjunctival eosinocytes was observed was selected, and the number of eosinocytes in 5 fields were counted which were not overlapped with one another under an optical microscope (magnifying power: 400). The mean of the counts of the 5 fields was calculated (cells/0.04 mm$^2$) to evaluate the medicine. The medicine was instilled in one eye at a dosage of 10 μl at 3, 2, 1 and 0.5 hour prior to challenge of conjunctivitis, respectively.

Results

Figure 2:
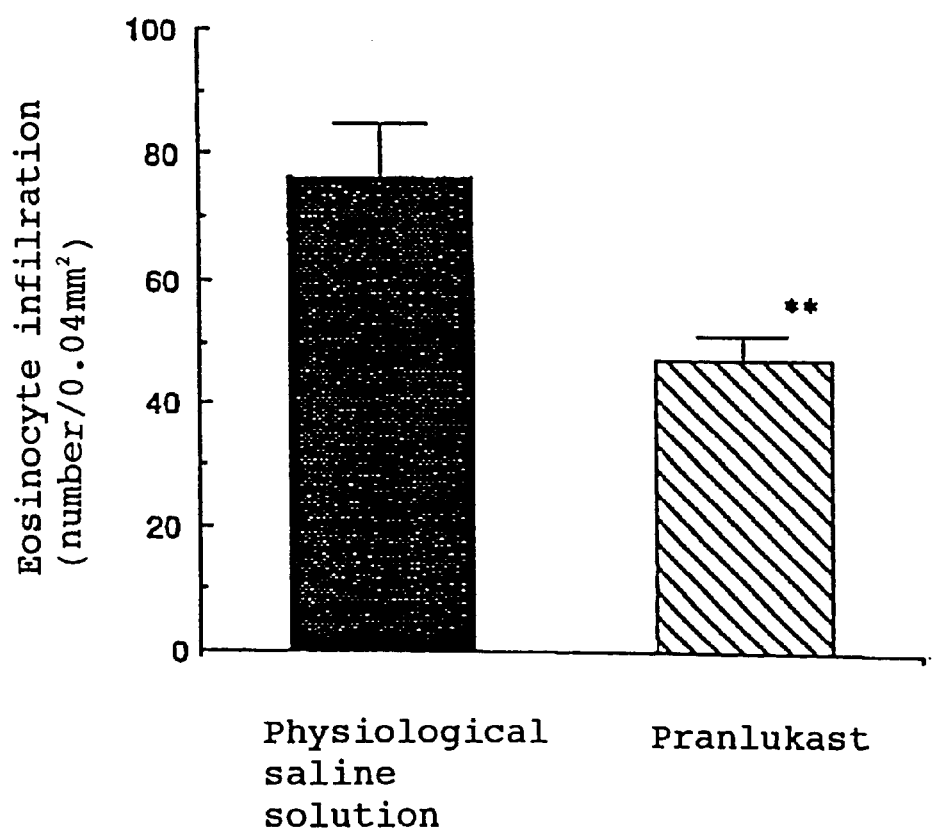
FIG. 2 is a graph illustrating the results of the test for inhibitory activity on conjunctival eosinocyte infiltration hereinafter.

The results are shown in FIG. 2.

FIG. 2 is a graph illustrating inhibitory effect of pranlukast on conjunctival eosinocyte infiltration in guinea pig allergic conjunctivitis. The values in the graph represent the mean ± standard error. The symbol ** represents the significant difference from physiological saline solution, $p<0.01$. As seen from FIG. 2, pranlukast showed significant inhibitory effect on conjunctival eosinocyte infiltration in the delayed type reaction.

PREPARATION EXAMPLE 1

Aqueous Solution

According to a conventional method, an aqueous solution for eye drops and nasal drops having the following formulation was prepared.

| Ingredient | Amount |
| --- | --- |
| Pranlukast | 0.1 g |
| Sodium dihydrogen phosphate 2 hydrate | 0.2 g |
| Polysorbate 80 | 4.0 g |
| Butylated hydroxytoluene | 0.01 g |
| Sodium edetate | 0.01 g |
| Benzalkonium chloride | 0.01 g |
| Sodium chloride | 0.9 g |
| 0.1 N sodium hydroxide | q.s. |
| Sterilized purified water | up to 100 ml |
| pH | 7.0 |

PREPARATION EXAMPLE 2

Aqueous Solution

According to a conventional method, an aqueous solution for eye drops and nasal drops having the following formulation was prepared.

| Ingredient | Amount |
| --- | --- |
| Pranlukast | 0.1 g |
| Sodium dihydrogen phosphate 2 hydrate | 0.2 g |
| Polyoxyethylene hydrogenated castor oil 60 | 2.0 g |
| Sodium edetate | 0.01 g |
| Benzalkonium chloride | 0.01 g |
| Boric acid | 1.5 g |
| 0.1 N sodium hydroxide | q.s. |
| Sterilized purified water | up to 100 ml |
| pH | 7.0 |

PREPARATION EXAMPLE 3

Aqueous Solution

According to a conventional method, an aqueous solution for eye drops and nasal drops having the following formulation was prepared.

| Ingredient | Amount |
| --- | --- |
| Pranlukast | 0.1 g |
| Sodium dihydrogen phosphate 2 hydrate | 0.2 g |
| Sodium edetate | 0.01 g |
| Benzalkonium chloride | 0.01 g |
| Tyloxapol | 4.0 g |
| Sodium chloride | 0.9 g |
| 0.1 N sodium hydroxide | q.s. |
| Sterilized purified water | up to 100 ml |
| pH | 7.0 |

PREPARATION EXAMPLE 4

Aqueous Solution

According to a conventional method, an aqueous solution for eye drops and nasal drops having the following formulation was prepared.

| Ingredient | Amount |
| --- | --- |
| Pranlukast | 0.1 g |
| Sodium dihydrogen phosphate 2 hydrate | 0.2 g |
| Polysorbate 80 | 4.0 g |
| Butylated hydroxytoluene | 0.01 g |
| Sodium edetate | 0.01 g |
| Benzalkonium chloride | 0.01 g |
| Boric acid | 1.5 g |
| Borax | 0.3 g |
| 0.1 N sodium hydroxide | q.s. |
| Sterilized purified water | up to 100 ml |
| pH | 7.0 |

PREPARATION EXAMPLE 5

Aqueous Suspension

According to a conventional method, an aqueous suspension for eye drops and nasal drops having the following formulation was prepared.

| Ingredient | Amount |
| --- | --- |
| Pranlukast | 1.0 g |
| Sodium acetate | 0.1 g |
| Hydroxypropylmethyl cellulose | 0.005 g |
| Sodium chloride | 0.9 g |
| Methyl p-hydroxybenzoate | 0.026 g |
| Propyl p-hydroxybenzoate | 0.014 g |
| 0.1 N hydrochloric acid | q.s. |
| Sterilized purified water | up to 100 ml |
| pH | 5.0 |

PREPARATION EXAMPLE 6

Aqueous Suspension

According to a conventional method, an aqueous suspension for eye drops and nasal drops having the following formulation was prepared.

| Ingredient | Amount |
| --- | --- |
| Pranlukast | 1.0 g |
| Sodium acetate | 0.1 g |
| HCO-60 | 0.1 g |
| Sodium chloride | 0.9 g |
| Methyl p-hydroxybenzoate | 0.026 g |
| Propyl p-hydroxybenzoate | 0.014 g |
| 0.1 N hydrochloric acid | q.s. |
| Sterilized purified water | up to 100 ml |
| pH | 5.0 |

PREPARATION EXAMPLE 7

Aqueous Suspension

According to a conventional method, an aqueous suspension for eye drops and nasal drops having the following formulation was prepared.

| Ingredient | Amount |
| --- | --- |
| Pranlukast | 1.0 g |
| Sodium acetate | 0.1 g |
| Tyloxapol | 0.1 g |
| Sodium chloride | 0.9 g |
| Methyl p-hydroxybenzoate | 0.026 g |
| Propyl p-hydroxybenzoate | 0.014 g |
| Chlorobutanol | 0.3 g |
| 0.1 N hydrochloric acid | q.s. |
| Sterilized purified water | up to 100 ml |
| pH | 5.0 |

PREPARATION EXAMPLE 8

Aqueous Suspension

According to a conventional method, an aqueous suspension for eye drops and nasal drops having the following formulation was prepared.

| Ingredient | Amount |
| --- | --- |
| Pranlukast | 0.5 g |
| Sodium acetate | 0.1 g |
| Hydroxypropylmethyl cellulose | 0.0025 g |
| Sodium chloride | 0.9 g |
| Methyl p-hydroxybenzoate | 0.026 g |
| Propyl p-hydroxybenzoate | 0.014 g |
| 0.1 N hydrochloric acid | q.s. |
| Sterilized purified water | up to 100 ml |
| pH | 5.0 |

PREPARATION EXAMPLE 9

Aqueous Suspension

According to a conventional method, an aqueous suspension for eye drops and nasal drops having the following formulation was prepared.

| Ingredient | Amount |
| --- | --- |
| Pranlukast | 0.1 g |
| Sodium acetate | 0.1 g |

-continued

| Ingredient | Amount |
| --- | --- |
| Hydroxypropylmethyl cellulose | 0.0005 g |
| Sodium chloride | 0.9 g |
| Methyl p-hydroxybenzoate | 0.026 g |
| Propyl p-hydroxybenzoate | 0.014 g |
| 0.1 N hydrochloric acid | q.s. |
| Sterilized purified water | up to 100 ml |
| pH | 5.0 |

PREPARATION EXAMPLE 10

Aqueous Suspension

According to a conventional method, an aqueous suspension for eye drops and nasal drops having the following formulation was prepared.

| Ingredient | Amount |
| --- | --- |
| Pranlukast | 1.0 g |
| Sodium acetate | 0.1 g |
| Methyl cellulose | 0.005 g |
| Sodium chloride | 0.9 g |
| Methyl p-hydroxybenzoate | 0.026 g |
| Propyl p-hydroxybehzoate | 0.014 g |
| 0.1 N hydrochloric acid | q.s. |
| Sterilized purified water | up to 100 ml |
| pH | 5.0 |

PREPARATION EXAMPLE 11

Aqueous Solution

According to a conventional method, an aqueous solution for an injectable preparation having the following formulation was prepared.

| Ingredient | Amount |
| --- | --- |
| Pranlukast | 0.1 g |
| Polysorbate 80 | 2.0 g |
| Sodium edetate | 0.01 g |
| Mannitol | 5.0 g |
| Citric acid | 0.1 g |
| 0.1 N sodium hydroxide | q.s. |
| Injectable distilled water | up to 100 ml |
| pH | 7.0 |

PREPARATION EXAMPLE 12

Aqueous Solution

According to a conventional method, an aqueous solution for an injectable preparation having the following formulation was prepared.

| Ingredient | Amount |
| --- | --- |
| Pranlukast | 0.1 g |
| Polyoxyethylene hydrogenated castor oil 60 | 2.0 g |
| Glycerin | 2.6 g |
| Torometamol | 0.1 g |

| Ingredient | Amount |
| --- | --- |
| 0.1 N hydrochloric acid | q.s. |
| Injectable distilled water | up to 100 ml |
| pH | 7.0 |

PREPARATION EXAMPLE 13

Aqueous Suspension

According to a conventional method, an aqueous suspension for an internal medicine having the following formulation was prepared.

| Ingredient | Amount |
| --- | --- |
| Pranlukast | 5.0 g |
| Polyvinyl pyrrolidone | 0.025 g |
| Sorbic acid | 0.2 g |
| Water | up to 100 ml |

PREPARATION EXAMPLE 14

Aqueous Suspension

According to a conventional method, an aqueous suspension for an internal medicine having the following formulation was prepared.

| Ingredient | Amount |
| --- | --- |
| Pranlukast | 5.0 g |
| Hydroxypropylmethyl cellulose | 0.025 g |
| Methyl p-hydroxybenzoate | 0.026 g |
| Propyl p-hydroxybenzoate | 0.014 g |
| Water | up to 100 ml |

PREPARATION EXAMPLE 15

Aqueous Suspension

According to a conventional method, an aqueous suspension for eye drops and nasal drops having the following formulation was prepared.

| Ingredient | Amount |
| --- | --- |
| Pranlukast | 1.0 g |
| Sodium acetate | 0.1 g |
| Hydroxypropylmethyl cellulose | 0.005 g |
| Ryutosugar ester S-1570 | 0.005 g |
| Sodium chloride | 0.9 g |
| Methyl p-hydroxybenzoate | 0.026 g |
| Propyl p-hydroxybenzoate | 0.014 g |
| 0.1 N hydrochloric acid | q.s. |
| Sterilized purified water | up to 100 ml |
| pH | 5.0 |

PREPARATION EXAMPLE 16

Aqueous Suspension

According to a conventional method, an aqueous suspension for eye drops and nasal drops having the following

| Ingredient | Amount |
| --- | --- |
| Pranlukast | 1.0 g |
| Sodium acetate | 0.1 g |
| Hydroxypropylmethyl cellulose | 0.005 g |
| Sodium lauryl sulfate | 0.1 g |
| Sodium chloride | 0.9 g |
| Methyl p-hydroxybenzoate | 0.026 g |
| Propyl p-hydroxybenzoate | 0.014 g |
| 0.1 N hydrochloric acid | q.s. |
| Sterilized purified water | up to 100 ml |
| pH | 5.0 |

PREPARATION EXAMPLE 17

Aqueous Suspension

According to a conventional method, an aqueous suspension for eye drops and nasal drops having the following formulation was prepared.

| Ingredient | Amount |
| --- | --- |
| Pranlukast | 1.0 g |
| Sodium acetate | 0.1 g |
| Hydroxypropylmethyl cellulose | 0.005 g |
| Polysorbate 80 | 0.01 g |
| Sodium chloride | 0.9 g |
| Methyl p-hydroxybenzoate | 0.026 g |
| Propyl p-hydroxybenzoate | 0.014 g |
| 0.1 N hydrochloric acid | q.s. |
| Sterilized purified water | up to 100 ml |
| pH | 5.0 |

What is claimed is:

1. An aqueous liquid pharmaceutical composition which comprises 4-oxo-8-[4-(4-phenylbutoxy)benzoylamino]-2-(tetrazol-5-yl)-4H-1-benzopyran or its hydrate and a surfactant.

2. The composition according to claim 1 further comprising at least one component selected from the group consisting of water-soluble cellulose derivatives and water-soluble vinyl polymers.

3. A method for inhibiting eosinocyte infiltration which comprises administering an effective amount of 4-oxo-8-[4-(4-phenylbutoxy)benzoylamino]-2-(tetrazol-5-yl)-4H-1-benzopyran or its hydrate to a subject in need of such inhibition.

4. A method for treating delayed type allergic conjunctivitis which comprises administering an effective amount of 4-oxo-8-[4-(4-phenylbutoxy)benzoylamino]-2-(tetrazol-5-yl)-4H-1-benzopyran or its hydrate to a subject in need of such treatment.

5. A method for improving solubility of 4-oxo-8-[4-(4-phenylbutoxy)benzoylamino]-2-(tetrazol-5-yl)-4H-1-benzopyran or its hydrate which comprises incorporating a surfactant therewith.

6. The method according to claim 5 which further comprises incorporating at least one component selected from the group consisting of water-soluble cellulose derivatives and water-soluble vinyl polymers therewith.

7. The method according to claim 5, wherein the surfactant is a member selected from the group consisting of nonionic surfactants, cationic surfactants and anionic surfactants.

8. The composition according to claim 1 which is an aqueous suspension comprising the benzopyran derivative or its hydrate and a surfactant, and further comprising at least one component selected from the group consisting of water-soluble cellulose derivatives and water-soluble vinyl polymers.

9. The composition according to claim 1, wherein the surfactant is a member selected from the group consisting of nonionic surfactants, cationic surfactants and anionic surfactants.

10. The composition according to claim 9, wherein the nonionic surfactant has a HLB of 10 to 18.

11. The composition according to claim 10, wherein the nonionic surfactant is a member selected from the group consisting of polyoxyethylene sorbitan fatty acid ester, polyoxyethylene hydrogenated castor oil, polyoxyethylene alkylphenyl formaldehyde condensate, polyoxyethylene polyoxypropylene block copolymer and sucrose ester of fatty acid.

12. The composition according to claim 9, wherein the cationic surfactant is selected from quaternary ammonium salts.

13. The composition according to claim 9, wherein the anionic surfactant is selected from alkyl sulfates.

14. The composition according to claim 2, wherein the water-soluble cellulose derivative is a member selected from the group consisting of methyl cellulose, carboxymethylcellulose, hydroxypropyl cellulose, hydroxyethyl cellulose and hydroxypropylmethyl cellulose.

15. The composition according to claim 2, wherein the water-soluble vinyl polymer is a member selected from the group consisting of polyvinyl pyrrolidone, polyvinyl alcohol and carboxyvinyl polymer.

16. The composition according to claim 9 which is an aqueous solution comprising the benzopyran derivative or its hydrate and the surfactant.

17. The composition according to claim 16 which contains at most 0.2 w/v % of the benzopyran derivative or its hydrate.

18. The composition according to claim 16 which contains 0.5 to 8 w/v % of the surfactant.

19. The composition according to claim 16 which contains 5 to 100 parts by weight of the surfactant per 1 part by weight of the benzopyran derivative or its hydrate.

20. The composition according to claim 16, wherein its pH is at lowest 6.

21. The composition according to claim 18 further comprising a stabilizer.

22. The composition according to claim 21, wherein the stabilizer is a member selected from antioxidants and chelating agent.

23. The composition according to claim 22, wherein the antioxidant is butylated hydroxytoluene.

24. The composition according to claim 22, wherein the chelating agent is sodium edetate.

25. The composition according to claim 8 which contains 0.01 to 5.0 w/v % of the benzopyran derivative or its hydrate.

26. The composition according to claim 8 which contains 0.00001 to 0.1 w/v % of the component selected from the group consisting of water-soluble cellulose derivatives and water-soluble vinyl polymers.

27. The composition according to claim 8 which contains 0.0001 to 0.1 part by weight of the component selected from the group consisting of water-soluble cellulose derivatives and water-soluble vinyl polymers per 1 part by weight of the benzopyran derivative or its hydrate.

28. The composition according to claim 8, wherein the surfactant is a member selected from the group consisting of nonionic surfactants, cationic surfactants and anionic surfactants.

29. The composition according to claim 8, wherein the nonionic surfactant is a member selected from the group consisting of polyoxyethylene sorbitan fatty acid ester, polyoxyethylene hydrogenated castor oil, polyoxyethylene alkylphenyl formaldehyde condensate, polyoxyethylene polyoxypropylene block copolymer and sucrose ester of fatty acid.

30. The composition according to claim 8, wherein the anionic surfactant is selected from alkyl sulfates.

31. The composition according to claim 8 which contains 0.0001 to 0.2 w/v % of the surfactant.

32. The composition according to claim 1 having eosinocyte infiltration inhibitory activity.

33. The composition according to claim 32 which is used for treatment of delayed type allergic conjunctivitis.

34. The composition according to claim 1 in the form of eye drops.

35. The composition according to claim 1 in the form of nasal drops.

36. The composition according to claim 1 in the form of an injectable preparation.

37. The composition according to claim 1 in the form of internal medicine.

* * * * *